(12) United States Patent
Kovac et al.

(10) Patent No.: US 6,663,641 B1
(45) Date of Patent: *Dec. 16, 2003

(54) ENDOSCOPIC SURGICAL INSTRUMENT FOR ROTATIONAL MANIPULATION

(75) Inventors: Tim J. Kovac, Los Gatos, CA (US); Michael F. Wei, San Mateo, CA (US)

(73) Assignee: Origin Medsystems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 394 days.

(21) Appl. No.: 09/704,396

(22) Filed: Nov. 2, 2000

Related U.S. Application Data (63) Continuation of application No. 08/949,080, filed on Oct. 10, 1997, now Pat. No. 6,171,316.

(51) Int. Cl.[7] .............................................. A61B 17/04
(52) U.S. Cl. ........................ 606/144; 606/148; 606/205
(58) Field of Search ................................. 606/205–208, 606/144, 148, 170, 180, 174; 600/104; 81/348, 385

(56) References Cited

U.S. PATENT DOCUMENTS

| | | | |
|---|---|---|---|
| 4,473,077 A | 9/1984 | Noiles et al. | |
| 4,485,817 A | 12/1984 | Swiggett | |
| 4,576,167 A | 3/1986 | Noiles | |
| 4,606,343 A | 8/1986 | Conta et al. | |
| 4,646,745 A | 3/1987 | Noiles | |
| 4,728,020 A | 3/1988 | Green et al. | |
| 4,935,026 A | 6/1990 | McFadden | |
| 4,944,443 A | 7/1990 | Oddsen et al. | |
| 5,005,749 A | 4/1991 | Aranyi | |
| 5,015,250 A | 5/1991 | Foster | |
| 5,037,433 A | 8/1991 | Wilk et al. | |
| 5,170,926 A | 12/1992 | Ruckdeschel et al. | |
| 5,192,288 A | 3/1993 | Thompson et al. | |
| 5,193,731 A | 3/1993 | Aranyi | |
| 5,196,023 A | 3/1993 | Martin | |

(List continued on next page.)

FOREIGN PATENT DOCUMENTS

| | | |
|---|---|---|
| EP | 0552 050 A2 | 1/1993 |
| EP | 0552 050 A2 | 10/1993 |

OTHER PUBLICATIONS

Publication/Brochure, Ethicon Endo–Surgery, Inc; Ets & Ets–Flex Endoscopic Linear Cutters.

*Primary Examiner*—Julian W. Woo
(74) *Attorney, Agent, or Firm*—Blakely, Sokoloff, Taylor & Zafman LLP (57) ABSTRACT

An endoscopic surgical instrument suitable for use with a needle-grasper having a rotational translation device for creating rotational motion at the distal end of the surgical instrument in a non 1:1 ratio to rotational energy imparted at the handle of the surgical instrument. The shaft of the surgical instrument has an articulated segment capable of remote adjustment to articulate the effector unit at the end of the surgical instrument. The effector unit may be a needle-gripper having an upwardly pointed V-shaped notch in a channeled upper jaw, a convex gripping surface on the lower jaw, such that grasping a curved suture needle between the upper and lower jaw serves to automatically orient the needle perpendicular to the needle-gripper with the curvature pointed down. Conically tapered edges on the upper jaw further facilitate this orientation. A reciprocal motion transmission occurs between the handle and the effector unit so that gripping the levers on the handle serves to operate a function in the effector unit. The device is suitable for manual operation by a surgeon performing endoscopic surgical manipulations directly and without the intervention of motors or the like.

11 Claims, 8 Drawing Sheets

U.S. PATENT DOCUMENTS

| | | |
|---|---|---|
| 5,197,649 A | 3/1993 | Bessler et al. |
| 5,205,459 A | 4/1993 | Brinkerhoff et al. |
| 5,211,650 A | 5/1993 | Noda |
| 5,222,962 A | 6/1993 | Burkhart |
| 5,224,948 A | 7/1993 | Abe et al. |
| 5,241,968 A | 9/1993 | Slater |
| 5,254,126 A | 10/1993 | Filipi et al. |
| 5,257,999 A | 11/1993 | Slanetz, Jr. |
| 5,258,005 A | 11/1993 | Christian |
| 5,271,543 A | 12/1993 | Grant et al. |
| 5,271,544 A | 12/1993 | Fox et al. |
| 5,275,322 A | 1/1994 | Brinkerhoff et al. |
| 5,282,806 A | 2/1994 | Haber et al. |
| 5,285,945 A | 2/1994 | Brinkerhoff et al. |
| 5,292,053 A | 3/1994 | Bilotti et al. |
| 5,320,635 A | 6/1994 | Smith |
| 5,333,773 A | 8/1994 | Main et al. |
| 5,355,897 A | 10/1994 | Pietrafitta et al. |
| 5,360,154 A | 11/1994 | Green |
| 5,364,002 A | 11/1994 | Green et al. |
| 5,370,134 A | 12/1994 | Chin et al. |
| 5,374,277 A * | 12/1994 | Hassler ............... 606/207 |
| 5,381,943 A | 1/1995 | Allen et al. |
| 5,383,888 A | 1/1995 | Zvenyatsky et al. |
| 5,387,221 A | 2/1995 | Bisgaard |
| 5,391,174 A | 2/1995 | Weston |
| 5,395,030 A | 3/1995 | Kuramoto et al. |
| 5,395,367 A | 3/1995 | Wilk |
| 5,403,342 A | 4/1995 | Tovey et al. |
| 5,405,073 A | 4/1995 | Porter |
| 5,409,498 A | 4/1995 | Braddock et al. |
| 5,417,203 A | 5/1995 | Tovey et al. |
| 5,417,699 A | 5/1995 | Klein et al. |
| 5,431,323 A | 7/1995 | Smith et al. |
| 5,431,662 A | 7/1995 | Nicholas |
| 5,431,669 A | 7/1995 | Thompson et al. |
| 5,439,156 A | 8/1995 | Grant et al. |
| 5,450,843 A | 9/1995 | Moll et al. |
| 5,452,836 A | 9/1995 | Huitema et al. |
| 5,454,819 A | 10/1995 | Knoepfler |
| 5,456,684 A | 10/1995 | Schmidt et al. |
| 5,465,894 A | 11/1995 | Clark et al. |
| 5,474,057 A | 12/1995 | Makower et al. |
| 5,474,568 A | 12/1995 | Scott |
| 5,478,003 A | 12/1995 | Green et al. |
| 5,478,344 A | 12/1995 | Stone et al. |
| 5,482,197 A | 1/1996 | Green et al. |
| 5,484,095 A | 1/1996 | Green et al. |
| 5,540,375 A | 7/1996 | Bolanos et al. |
| 5,545,148 A | 8/1996 | Wurster |
| 5,549,637 A | 8/1996 | Crainich |
| 5,560,532 A | 10/1996 | DeFonzo et al. |
| 5,571,115 A | 11/1996 | Nicholas |
| 5,575,799 A | 11/1996 | Bolanos et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,609,601 A * | 3/1997 | Kolesa et al. ............... 606/170 |
| 5,620,415 A | 4/1997 | Lucey et al. |
| 5,620,447 A | 4/1997 | Smith et al. |
| 5,624,381 A | 4/1997 | Kieturakis |
| 5,626,587 A | 5/1997 | Bishop et al. |
| 5,634,584 A | 6/1997 | Okorocha et al. |
| 5,636,780 A | 6/1997 | Green et al. |
| 5,639,008 A | 6/1997 | Gallagher et al. |
| 5,643,294 A * | 7/1997 | Tovey et al. ............... 606/148 |
| 5,662,662 A | 9/1997 | Bishop et al. |
| 5,667,476 A | 9/1997 | Frassica et al. |
| 5,673,840 A | 10/1997 | Schulze et al. |
| 5,674,230 A | 10/1997 | Tovey et al. |
| 5,680,982 A | 10/1997 | Schulze et al. |
| 5,683,349 A | 11/1997 | Makower et al. |
| 5,692,668 A | 12/1997 | Schulze et al. |
| 5,725,536 A | 3/1998 | Oberlin et al. |
| 5,732,871 A | 3/1998 | Clark et al. |
| 5,741,276 A | 4/1998 | Poloyko et al. |
| 5,782,859 A | 7/1998 | Nicholas et al. |
| 5,794,834 A | 8/1998 | Hamblin et al. |
| 5,797,537 A | 8/1998 | Oberlin et al. |
| 5,855,583 A | 1/1999 | Wang et al. |
| 6,102,850 A | 8/2000 | Wang et al. |
| 6,132,441 A | 10/2000 | Grace |
| 6,223,100 B1 | 4/2001 | Green |
| 6,244,809 B1 | 6/2001 | Wang et al. |
| 6,246,200 B1 | 6/2001 | Blumenkranz et al. |

* cited by examiner

ENDOSCOPIC SURGICAL INSTRUMENT FOR ROTATIONAL MANIPULATION

This is a Continuation of application Ser. No. 08/949,080 filed Oct. 10, 1997 now U.S. Pat. No. 6,171,316.

BACKGROUND OF THE INVENTION

1. Field of the Invention

This invention relates to a surgical instrument for remote manipulation and more particularly to an instrument for use in endoscopic surgery, the instrument having an articulated shaft and transmitting rotational motion to the distal end of the instrument.

Minimally invasive surgery (MIS) such as laparoscopic, endoscopic, hysteroscopic, and arthroscopic surgery (referred to hereafter generally as endoscopic surgery), is becoming more widely used because it is less traumatic to the patient, generally involves less hospitalization time, less discomfort and less risk to the patient, and is usually less costly than traditional open surgery.

Such a procedure is typically performed by making a small incision in the patient which provides access to the area to be treated. A trocar sheath may be inserted in the incision and an airtight seal around the trocar established. The area under the skin which is to be treated may be dissected from surrounding tissue by, for example, balloon dissection. With or without dissection, the area may be expanded slightly as by insufflation with $CO_2$ in order to create a cavity within which to perform the surgical procedure. Access to this cavity may be through by one or more trocar sleeves which may be configured to permit the slidable insertion of endoscopes and surgical instruments without compromising the air tight seal around the trocar sheath. Each such endoscopic surgical instrument is often inserted through a different incision.

The endoscopic surgery is generally preformed using elongate instruments slidably inserted through the trocar sleeves, or if the endoscopic surgery is performed in a naturally occurring body cavity, such as the uterus, the instruments may be inserted through a relatively narrow body orifice such as the cervix. The manipulations being performed by the instruments during endoscopic surgery are generally observed through an endoscope which may be inserted through a separate trocar into the operating cavity. Alternatively, the endoscope may be contained within a surgical tube which also contains surgical instruments. In any event, the operator must perform the surgical manipulations using an effector unit, such as a scalpel or needle gripper on the end of the surgical instrument remotely located from the operator's hands and confined within a relatively small cavity created for the operation. The manipulation must be performed while observing the procedure with an endoscope. The image from the endoscope is often displayed on a video screen and generally results in an image having little or no depth perception.

Of particular interest is suturing or tying knots during endoscopic surgery. Suturing and tying knots using remote effector units while observing the manipulation through an endoscope is very challenging for the surgeon. Traditionally the surgical instruments employed to perform endoscopic suturing may include simple endoscopic needle holders, a variety of specialized needle drivers, and motorized telesurgical systems. The problems associated with remote knot tying have lead to the development of such instruments and devices as pre-tied knots, ultrasonic welded knots, beads swaged in such a way as to facilitate the crimping of sutures together, and, again, motorized systems. Most of the methods described above are limited in use to interrupted rather than continuous suturing. Some, for example the telesurgical system, require complex instrumentation and may not be available for all endoscopic procedures, especially the simpler procedures. In addition, the motorized systems generally limit or eliminate the kinesthetic ability of the surgeon to sense and directly anipulate the suture or needle.

One particularly cumbersome technique that is often used to achieve suturing using traditional endoscopic instruments, is the "hand off" of the needle from one instrument to another. This technique exacerbates the difficulty of remote manipulation in limited space and restricted visualization with the requirement of coordination of two or more instruments. This technique involves insertion of the suturing needle by the operative instrument into the tissue to be sewn. The needle is then pushed forward, driving the needle through the tissue. A second instrument, may apply counter-pressure to the tissue at the location where the sharp tip of the needle will emerge at the end of the stitch. This entrance drive of the needle through the tissue generally involves a rotating motion, particularly critical where a sharply curved needle is used.

Once the tip of the needle emerges from the tissue, it is extracted by the assisting instrument grasping the tip of the needle and pulling. The principal needle driver releases its grip on the needle and may be placed beside the location where the needle is exiting the tissue to act as a counter-pressure instrument in place of the assisting instrument which is now pulling the needle from the tissue, pushing the tissue down while the needle is being pulled out by the assisting instrument. As with the entrance drive, the extracting motion often involves significant rotation in order to avoid tearing the tissue, particularly with a sharply curved needle.

After the needle is extracted, the trailing suture may be pulled through the tissue, again with the use of two cooperating instruments, each pulling at the suture sequentially until the correct amount of suture has been pulled through the tissue.

For single stitch technique, the suture is then tied, itself a complex procedure especially where performed with a viewing system having very limited depth perception. When continuous sewing is performed, the needle is grasped by the principal operative instrument after the suture is pulled through the tissue as desired in preparation to performing the sequence again to form a second stitch. First, the assisting instrument grasps the fully extracted needle and holds it in an optimal position for the principal needle driver to grasp. The assisting second instrument generally must grasp the needle near the tip so that the principal needle driver can grasp the needle far enough to the rear of the sharp tip to provide adequate length to pass the needle through the tissue layers during the next entrance drive so that enough of the needle tip will exit to be grasped by the assisting instrument. The assisting instrument must hold the needle at an appropriate orientation so that the principal needle driver will grasp the needle at the proper orientation for making the next entry into the tissue. Since traditional endoscopic instruments have a limited range of rotation at the distal end relative to the handle, this orientation is critical. Once again, this needle insertion and drive through the tissue, and subsequent extraction of the needle at the end of the stitch, requires significant rotational motion. It is often desirable during such procedures to hold the forearms of the operator relatively stationary, the rotational motion imparted by the hands of the operator rotating at the wrists may be insufficient to successfully accomplish the stitching.

The efforts required for a successful hand-off and continuous suturing highlights a number of problems with current endoscopic tools. It is a problem to properly orient the needle relative to the needle gripper. For effective suturing, the curved needle should be grasped by the principal needle driver with the needle extending perpendicular to the grasper and with a sufficient length of the front end of the needle protruding so that the needle may be inserted into the tissue. This is very difficult when the operator is viewing the procedure with limited or no depth perception.

It is also a problem to provide sufficient rotation after grasping the needle to rotate the needle to insert the tip into the desired location to start the stitch. This is particularly problematic given the limited rotational motion of the human wrist, or with mechanical devices such as side mounted rotational knobs that are sometimes provided to achieve rotation at the distal end at an endoscopic tool. The requirement for two instruments to carry out this technique may also create the need for additional incisions, further complicating the procedure and adding additional trauma, risk and expense to the procedure.

Another problem presented by the use of some current endoscopic instruments with needle grabbers is access to a location that is at an angle to the end of a straight surgical instrument. An endoscopic surgical instrument must generally be straight to be inserted through a trocar sleeve. Although some angle of reach is available by twisting the trocar in the patient's body and thereby pointing the instrument in slightly different directions, this is obviously limited by such considerations as the need to keep the trocar incision relatively airtight if the operating cavity is insufflated, and the need to avoid traumatizing the patient unnecessarily. Since movement of the instrument and the twisting and straining of the trocar at the site of the incision can threaten the airtight seal and be traumatic to the patient, it would be preferable to reach locations within the operating area by articulating the end portion of the surgical instrument without having to twist the instrument or the trocar at the site of the incision. Some form of articulation within the instrument shaft, preferably near the distal end of the instrument shaft, with the articulation being controllably adjustable by the operator after insertion of the instrument, is advantageous.

Various endoscopic surgical instruments, such as surgical staplers, and surgical retraction devices for use in endoscopic procedures, are disclosed in the prior art. See, for example, U.S. Pat. No. 5,192,288, directed to a surgical clip applier and U.S. Pat. No. 5,431,669, directed to a surgical clip applier with distal hook. Also disclosed in the art are endoscopic surgical instruments having knobs for the adjustment of angles of articulation and rotation of a staple applier as disclosed in U.S. Pat. No. 5,662,662, directed to a surgical instrument and method, and U.S. Pat. No. 5,607,095, directed to an endoscopic surgical instrument with pivotable and rotatable staple cartridge.

Graspers for suture needles are also shown in the prior art. For example, U.S. Pat. No. 5,015,250, directed to a medical instrument for driving a suture needle, discloses a needle driver instrument suitable for use with a trocar sheath in operative endoscopic surgical procedures for holding and driving a curved suture needle.

Given the needs of those operating in the environment of endoscopic surgery, it would be desirable to provide a surgical instrument directly responsive to hand and forearm rotation which is capable of imparting rotational motion in a non 1:1 ratio to an effector unit such as a needle gripper. It would also be desirable to provide a needle gripper which would automatically orient a curved suture needle. Additionally, it would be desirable to provide a needle gripper which could be remotely operated by, for example, operating a reciprocating rod at the handle of a surgical instrument to open and close the jaws of a needle gripper at the distal end of an elongate shaft on the surgical instrument. Moreover, it would also be desirable to provide a surgical instrument such as a needle gripper that could simultaneously be manipulated in multiple ways, such as opening and closing and simultaneously rotating, by the same hand of the operator, thus providing dynamic control over the manipulation of effector unit such as a needle gripper.

SUMMARY OF THE INVENTION

According to the present invention an improved surgical instrument for endoscopic surgery is provided for performing surgical manipulations requiring rotational motion of an effector unit a non 1:1 ratio to the rotational movement applied by the hands of the surgeon to the handle. For example, translating the rotational movement applied by direct rotation of the hands of the surgeon through a planetary gear system may allow the surgeon to rotate a small diameter (e.g., 5 mm) tool such as a needle gripper at the distal end of an endoscopic surgical tool sufficiently to perform a surgical manipulation within the relative limited space generally available in an endoscopic procedure. Moreover, the invention provides a surgical instrument having direct rotational translation without employing a motor, or a knob that must be turned by the fingers, thereby providing surgical manipulation that is kinesthetically similar to the rotational movement provided by the wrist action of the surgeon but in degree may be greater than or less than the rotational motion available directly from the wrist of the surgeon. In one embodiment, the surgical instrument provides reciprocating motion which is supplied to the effector unit by squeezing the same handle used to impart the rotational motion through the translation mechanism to the effector unit, thereby allowing the surgeon to simultaneously operate the effector unit, as in opening and closing the jaws of a needle gripper, while causing rotation. This dynamic control with the same hand adds advantageously to the control by the surgeon.

Because of the possibility for exaggerated rotational movement, the surgeon is able to keep his forearms very still while rotating only his wrists and thereby achieves adequate rotation at the distal end of the tool in order to perform a manipulation that requires a greater degree of rotation than would normally be available from simply his wrist rotation. Conversely, he is able to perform very delicate rotational motions at the distal end if the rotational motion at the distal end is less than a ratio of 1:1 to the rotational motion applied to the handle.

The rotational action of the surgeon's wrists provides rotational motion directly to the effector unit. The familiar kinesthetic control by the surgeon over the effector unit, a situation often desirable in employing the manual skill of the surgeon. This may be particularly critical where the surgeon is performing a dynamic manipulation such as sewing rather than merely positioning a mechanical device such as a staple cartridge.

The instrument of the preferred embodiment is provided with an articulated section, which provides for angulation of the distal end portion of the instrument inside the patient so that the working end of the instrument can be directed to a location that is not in a straight line with the upper portion of the shaft of the instrument. This may be particularly important where the shaft of the instrument is inserted through a trocar sleeve and angular motion is somewhat restricted. The articulated portion is remotely adjustable so that the amount and direction of the curvature can be adjusted by the operator to locate the working end of the instrument with an effector unit such as a needle gripper within the operating area while observing the instrument in the operating area and thus position the working end as desired in direct relation to the tissue to be treated, for example, sutured.

A means is provided for smooth transmission of rotational motion around any curve in the articulated section so that rotation applied by the operator can be transmitted to the distal portion to rotate an actuary unit, for example, a surgical needle gripper. The needs for transmitting rotational motion may be a sheathed cable, a jointed hex rod with pins, other pinned joint linkage, or other similar device for smoothly transmitting rotational motion around a curve.

The invention may be provided with an effector unit, whether permanent, detachable or interchangeable at its distal end. Such effector units may include cannulas, cameras, staplers, ligation devices, forceps, drills, cutting devices, scalpels, clamps, illumination devices and the like. In the aforedescribed surgical effector unit, a surgical instrument of the invention may be employed to provide the desired rotational movement of the articulatable tip of the surgical instrument shaft.

One novel effector unit that is advantageously usable with the surgical instrument is a novel needle gripper which functions to securely grasp a curved surgical needle while simultaneously placing the needle in a predetermined orientation for performing stitching by use of the rotational motion of the surgical instrument of the invention. In a preferred embodiment, the needle gripper is configured having two jaws, a first jaw having a U-shaped channel therein, which first jaw has a V-shaped side face. The second jaw has a gripper surface opposed to the channel in the first jaw, which gripper surface is an elongate linear convex surface. As the jaws close over a curved suture needle having a round cross-section, that needle is oriented so that it is gripped perpendicular to the jaws and is rested in the apex of the V notch in the one jaw and curved pointing downward over the gripper surface so that the needle arc is curved around the convex surface of the gripper surface. The edges of the legs of the U-shaped channel are conically tapered so that, as the curved needle is gripped between the convex gripper surface on the anvil and the conically tapered edges of the upper jaw channel, it assumes the orientation pointing downward as described above.

The invention generally includes a handle portion rotationally attached to a rotational motion translator such as a planetary gear mechanism, an elongate shaft attached to the rotational motion translator, an articulated section at the distal portion of the elongate shaft, and an effector unit such as a suture needle gripping device attached to or integrally incorporated onto the distal end of the shaft beyond the articulated section. A means for smoothly transmitting rotational energy from the rotational translation means, including through the articulated section, even when the articulated section is curved or angled, to the effector unit is provided. That may include a sheathed cable, or multiple jointed hex-rod with pins, and may include the elongate shaft. Alternatively, the elongate shaft may be hollow and contained within it the rotational transmitting means.

A reciprocating motion transmitter is also contained as part of the instrument. It may generally be actuated by motion of a lever or levers at the handle and reciprocates a motion carrier which may be contained within the elongate shaft to transmit reciprocating motion to the effector unit. This may be used, for example, to open and close the jaws of the needle gripper.

Other features and advantages of the invention will become apparent from the following detailed description, taking into conjunction with the accompanying drawings, which illustrate, by way of example, the features of the invention.

DETAILED DESCRIPTION

As shown in the drawings for purposes of illustration, the invention is embodied in a surgical instrument of the type having a handle portion 10 for gripping by the hands of a surgeon, a rotational motion translator 50 for translating rotational motion imparted to the handle, into rotational motion imparted to a torque transmitting tube 29 which serves to transmit rotational motion from the translator through the outer shaft portion 100. The outer shaft portion extends from the rotational motion translator to an effector unit 140 and includes an articulated section 120. The effector unit 140 may be a needle gripper for grasping and driving a curved needle during suturing. Alternatively the effector unit may be any of a variety of tools as listed in exemplary form in the summary section above.

Figure 1:
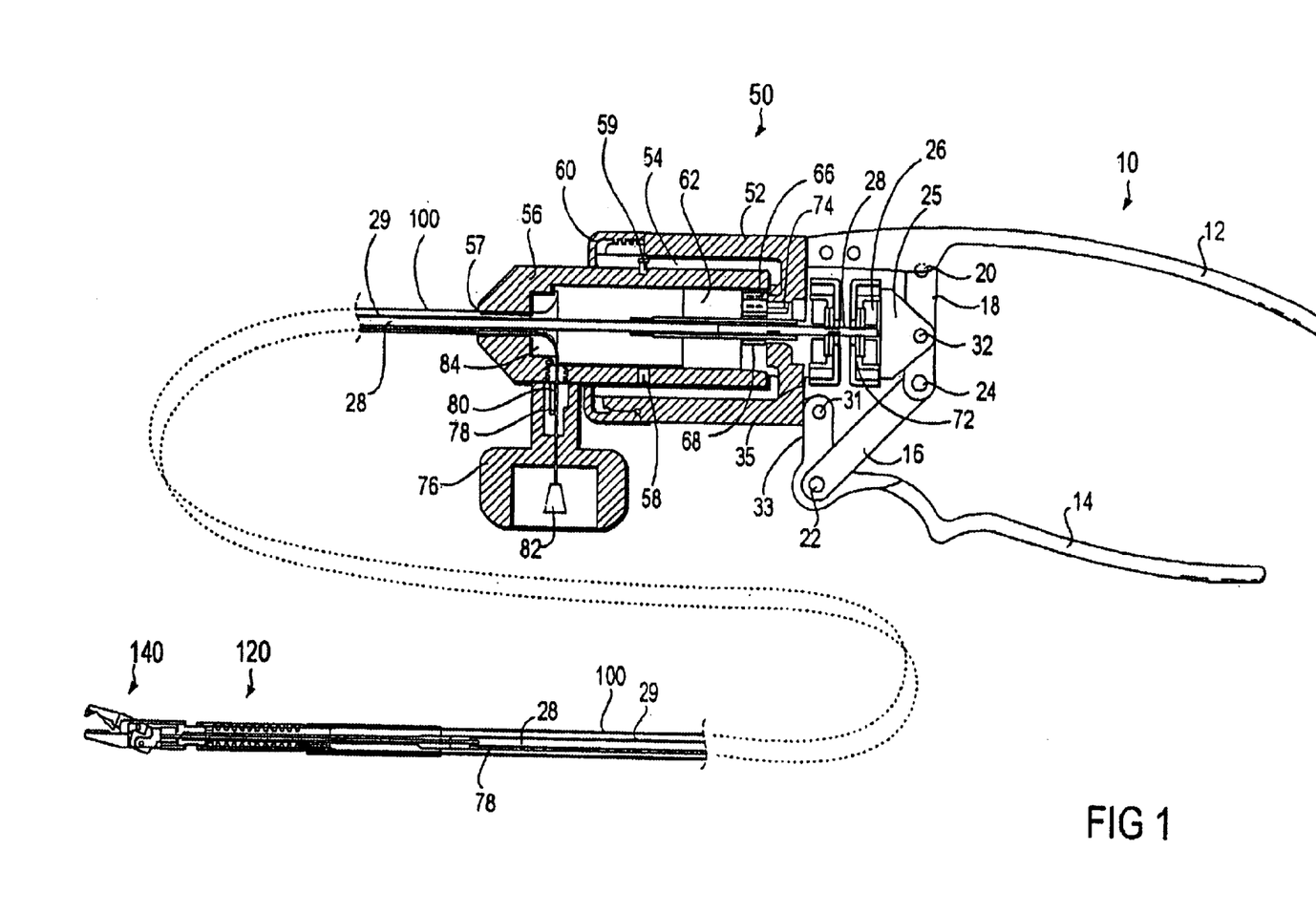
FIG. 1 is a cross-sectional view of a surgical instrument embodying the invention.

Referring in general to FIG. 1 for purposes of illustration, the handle portion 10 is comprised of an upper gripping lever 12, and a lower gripping lever 14 connected to the upper gripping lever by means of a lower connector link 16 and an upper connector link 18. The upper connector link is pivotally attached at one end to the upper gripping lever at pivot pin 20 and to the lower connector link at pivot pin 24. The lower connector link is pivotally attached to the lower gripping lever at pivot pin 22 and to the upper connector link at pivot pin 24. Gripping levers 12, 14 may be biased apart, so that when squeezed they will be compressed toward each other, but when released they will move away from each other. The gripping mechanism may be provided with a ratchet or other catch mechanism whereby the return travel of the gripping levers may be prevented or restrained until released by the operator. By this means, the effector unit may be maintained in the condition having the tension rod 28 retracted, as with the jaws 142, 144 of FIG. 12, of the needle gripper 140 closed, without constant manual pressure from the operator, until the operator releases the gripper levers by intentionally releasing the ratchet or catch mechanism. Downward movement of the lower gripping lever is limited when an end surface 33 of the lower gripping lever contacts on end surface 35 of the carrier.

A holder 25 is pivotally attached to the upper connector link 18 at centrally located pivot pin 32. A thrust bearing nut 26 of a tension rod 28 is contained within the holder. The tension rod is firmly affixed to the nut which, in turn, is firmly contained within the holder 25 so that compression of the gripper levers towards each other functions to pivot the upper connector link and lower connector link 16 so that the connector links 18, 16 close in scissor like fashion, reciprocating the holder rearward. This in turn functions to pull the tension rod in a reciprocating motion rearward.

Figure 2:
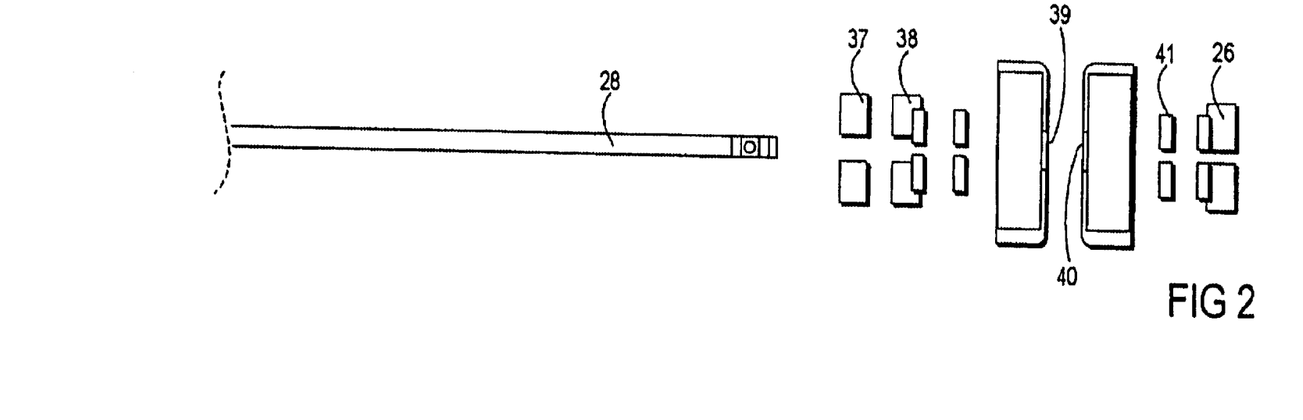
FIG. 2 is an exploded view of the tension rod and head assemble of the surgical instruction of FIG. 1.
Figure 3:
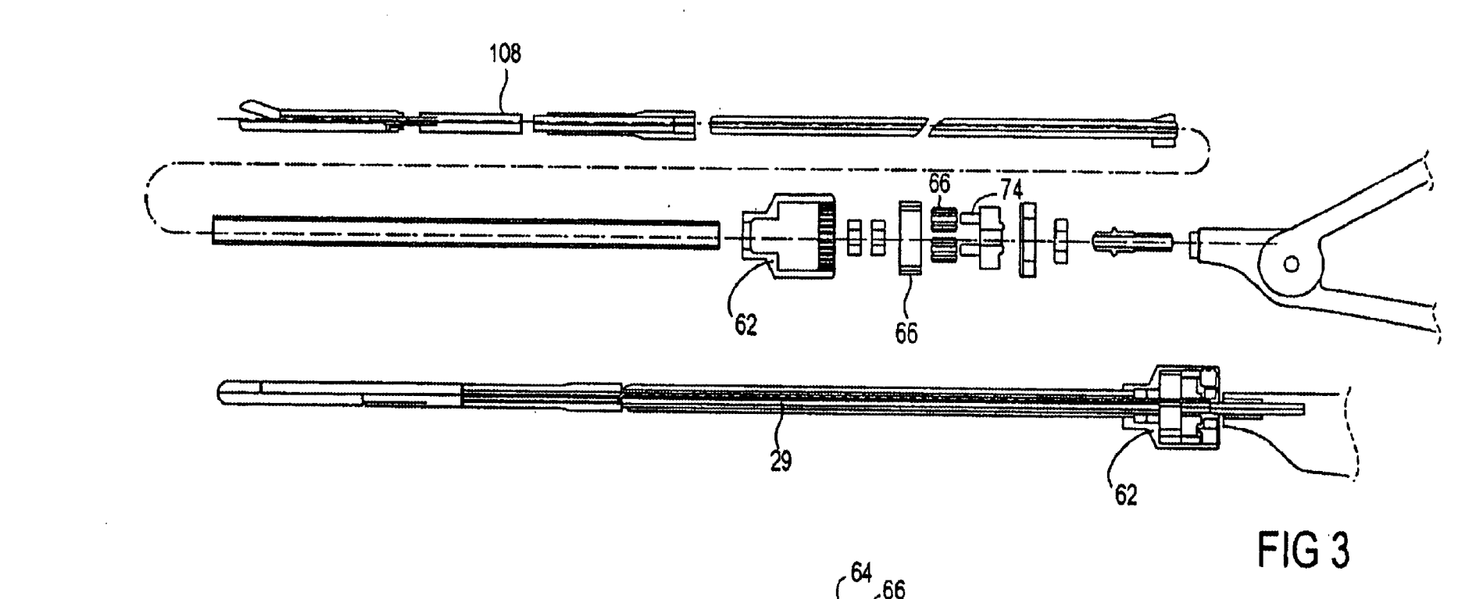
FIG. 3 is an exploded view of an embodiment of the invention.
Figure 4:
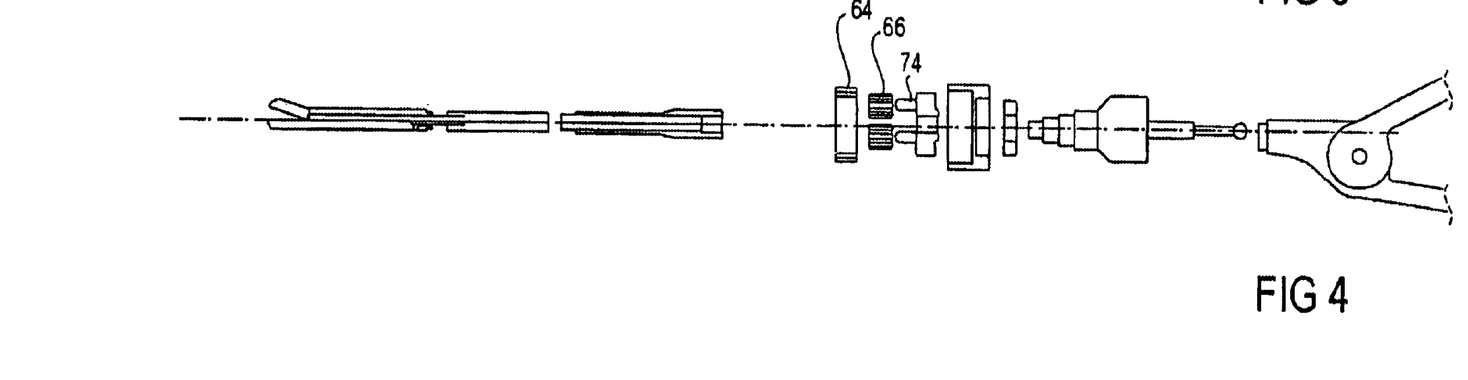
FIG. 4 is an exploded view of an embodiment of a portfolio of the invention.

Referring generally to FIG. 2, which is an exploded view of the tension rod 28 and head assembly 31, the tension rod 28 is inserted through thrust bearings 37, 38, orifice 39 and orifice 40, bearing 41 and is firmly attached within the thrust bearing nut 26 by, for example, screw threads 33. By means of this arrangement it will be seen that compression of the handles functions to reciprocate the tension rod.

Referring again to FIG. 1, the upper handle 12 is fixedly attached to a carrier 52 which comprises the outer section of rotational motion translator 50. The lower gripper handle 14 is pivotally attached at pivot pin 31 to the carrier. The carrier has a generally cylindrical interior cavity. Contained within the interior cavity is a bearing 54 which is a generally tubular, contact with the outer surface of bearing 54 in the carrier's cylindrical inner surface, and with inner surface of bearing 54 in contact with the generally tubular outer surface of a nose piece 56. The bearing may be secured to the nose piece by one or more pins 58, 59. The carrier may be secured longitudinally relative to the bearing 54 and thus to the nosepiece 56 by means of a housing cap 60 which is generally annular in shape and serves to be securely affixed to the forward end of the carrier to be angled over the distal end of the bearing 54 and to encircle the nose piece. Smooth rotation is thereby facilitated because, as the carrier is rotated, the nose piece is stationary relative to the carrier, the carrier rotates with the inner surface in contact with the outer surface of the bearing 54 while the gripper angle is rotating around the end surface of the bearing 54.

The nose piece 56 is generally tubular in shape. At its distal end it is attached to the shaft 100. At its proximal end it contains a planetary gear mechanism.

Figure 5:
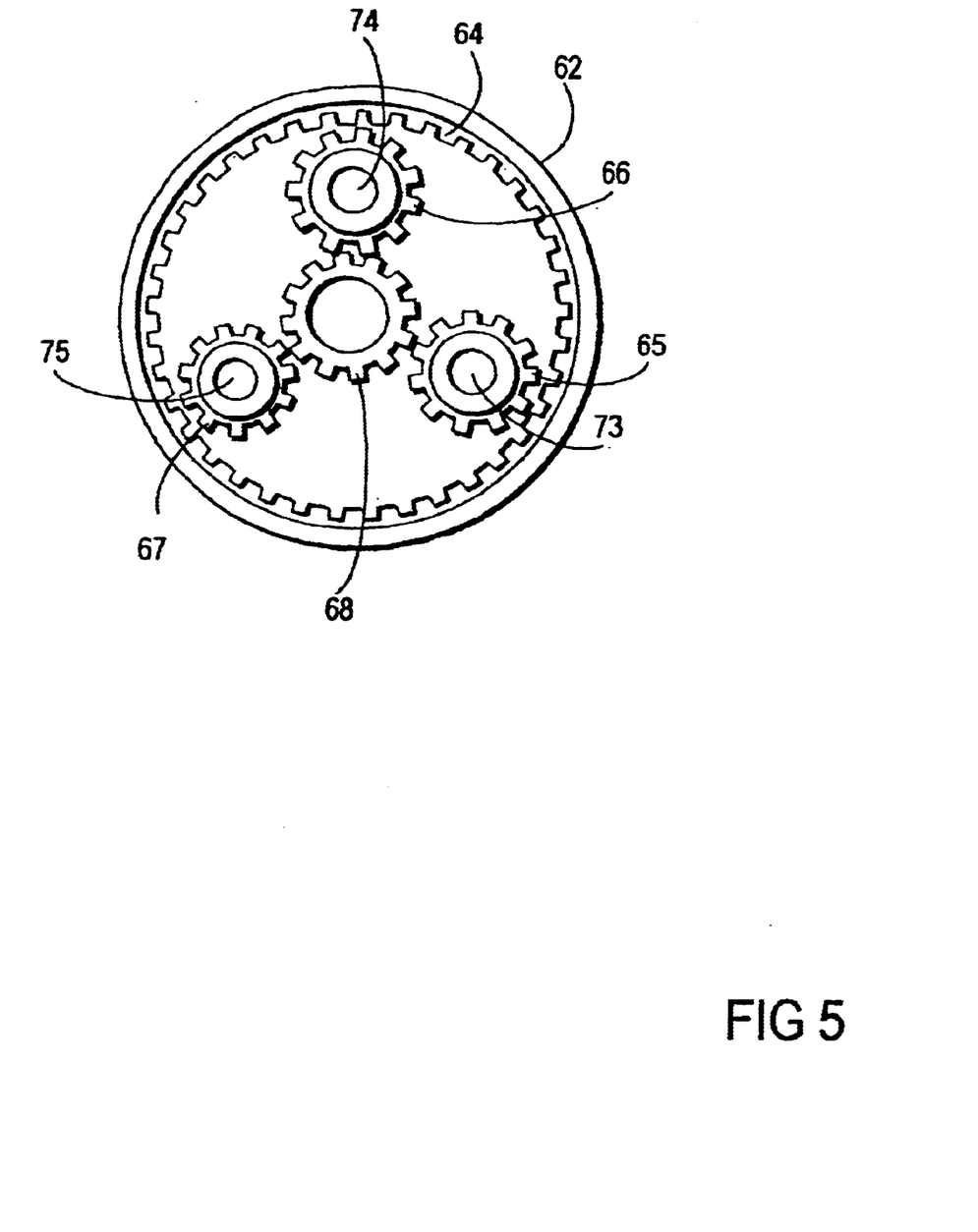
FIG. 5 is an end cross-sectional view of the planetary gear mechanism of an embodiment of the invention.

Referring generally for purposes of illustration to FIGS. 1 and 5, the planetary gear mechanism comprises a planetary housing 62 configured around the internal circumference of the planetary housing are the teeth of a ring gear 64. Meshed with the ring gear are three planetary gears 65, 66, 67. The planetary gears rotate around rotation pins 73, 74, 75. The planetary gears are, in turn, meshed with the sun gear 68. It may therefore be seen that rotation of the carrier 52 relative to the nose piece 56 will cause the ring gear to rotate, transferring rotational motion through the sun gear. In the configuration shown, the rotation is translated at a ratio of 4:1. That is, a 90° rotation of the carrier relative to the nose piece translates into a 360° rotation of the sun gear;

Sun gear 68 is attached to torque transmitting tube 29. The torque transmitting tube may be, for example, braided wire or mesh. Rotation of sun gear causes rotational motion in the torque transmitting tube which is transmitted in an essentially 1:1 ratio smoothly to the effector unit 140 at the distal end of shaft 100.

Contained within the torque transmitting tube 29 is tension bar 28. The tension rod is slidably contained within the torque transmitting tube 29 and is slidably contained within the sun gear 68, and extends through the sun gear to the thrust bearing nut 26. As previously described, compression of the upper gripping lever 12 and lower gripping lever 14 functions to withdraw the thrust bearing nut rearwardly and slidably move the torsion rod rearward within the torque transmitting tube. Bearing 72 serves to minimize friction as a result of the reciprocating motion of torsion rod 28.

The nose piece 56 has mounted thereon an articulation adjustment knob 76. The articulation adjustment knob may be rotated to tighten or loosen an adjustment cable 78 by means of a threaded hollow shaft 80 and wire collet 82. This tightening or loosening of the cable 78 functions to adjust the amount of curvature of the articulating section 120 as described in greater detail below. The movement of the cable into the interior of the shaft 100 through an aperture 57 in the nose piece 56 is facilitated as the cable runs across friction reducing bearing 84.

The elongate shaft 100 may be in the form of a smooth hollow tube made of, for example, surgical stainless steel. The smooth outer skin of the tube may be particularly advantageous for an instrument to be inserted slidably contained within a trocar cannula in an endoscopic procedure. The tube serves as a conduit for the torsion rod 28, the torque transmitting tube 29 and the articulation adjustment cable 78.

For purposes of creating rotational motion as the effector unit by rotation applied by the hands of the surgeon, the carrier 52 and thus the ring gear 64 or rotated relative to the nose piece 56 and thus rotated relative to the sun gear and torque transmitting tube. The nose piece may be held in one hand while the other hand rotates the handle portion. Likewise, the nose piece may be fixed to the trocar cannula as with a spline or keyed slot (not shown). Rotation of the handle 10 may then occur relative to the nose piece with the surgeon having to grip the nosepiece with his hand. Alternatively, a gimble (not shown) may be provided wherein the nose piece is rotationally restrained relative to the handle. Depending upon the preference of the surgeon, such an arrangement will be provided to allow the surgeon to create rotational manipulation by rotation of his wrists and to kinesthetically mimic direct rotational manipulation of the effector unit during surgical procedures. In a dynamic situation such as sewing, as opposed to a relatively static situation wherein an effector unit is positioned first and subsequently functions while stationary, as in a stapler, this permits the surgeon to perform surgical tasks such as sewing and knot tying wherein dynamic motion directly under the control of the surgeon's hands is necessary.

The elongate shaft 100 contains at its distal region the articulated section 120. Referring generally to FIG. 6 through FIG. 10, the articulated section 120 is in the general form of a slotted tube 121. The tube has an unsegmented proximal length 122. Distal of the unsegmented proximal length are a series of ribs 124 interspersed between cutout sections 126. Along the length of the tube and located 180° apart with respect to each other are spines 128, 129. The width of the spine increases by 0.001 inches with each successive cut, beginning with a width of 0.024 inches at the initial cut 130 and ends with the 12th spine area being 0.035 inches wide at 132.

Figure 10:
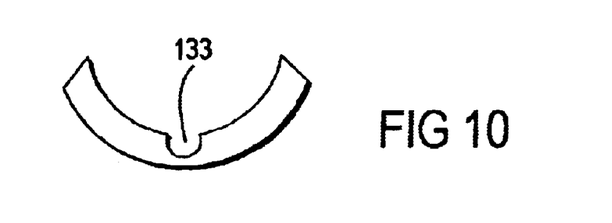
FIG. 10 is a partial cross-section of the segmented tube of an embodiment of the invention.
Figure 11:
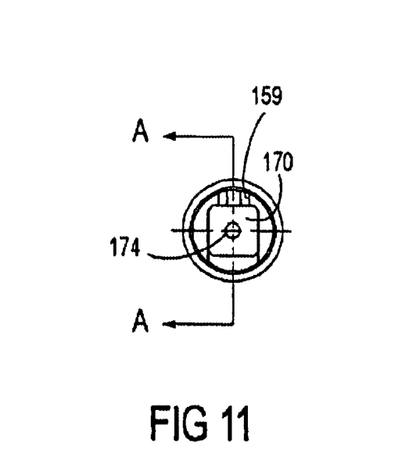
FIG. 11 is a rear plan view of the needle gripper of an embodiment of the invention.

Located along the length of the interior of one side of the tube 121 is cable channel 133. The cable channel is located approximately equal distance from each spine, that is 90° around the tube from each spine. The cable channel 133 contains the articulation adjustment cable 78. That cable is affixed to the distal end of the articulated section. As the wire is withdrawn, it causes the articulated section to compress on the side containing the wire and curve in that direction.

Figures 7, 8:
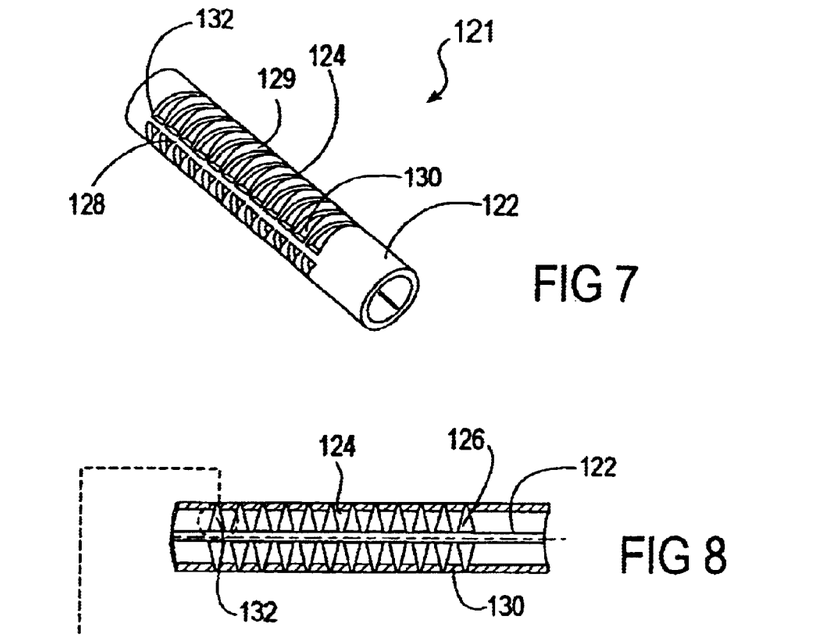
FIG. 7 is a perspective view of a segmented tube of the articulated section of an embodiment of the invention.
FIG. 8 is a top plan view of a segmented tube of the articulated section of an embodiment of the invention.
Figure 9:
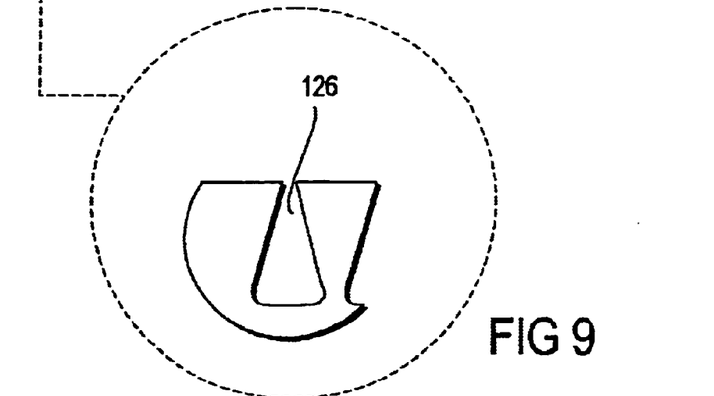
FIG. 9 is a top plan view of section C in FIG. 8.

The cut-out section 126 between ribs is generally angular with the greatest distance between adjacent ribs generally located immediately adjacent the spines and the narrowest distance located on the circumference midway between the spines. The shape may be formed, for example, by cutting the tube slightly greater than perpendicular to the tube's longitudinal axis until the cut reaches the edge of the spine, continuing the cut for a short distance along the longitudinal axis of the tube perpendicular to the spine, and then cutting outward at an angle slightly less than perpendicular to the longitudinal axis of the tube. This results in a cut out section, which when viewed directly from above as in FIG. 8, is roughly triangular in shape with a truncated apex.

The segmented articulated section may be covered on its exterior by an elastomeric smooth membrane 125. Such smooth covering is advantageous for cleanliness and safety. The elastomeric nature of the membrane allows curvature of the articulated section.

Figure 16:
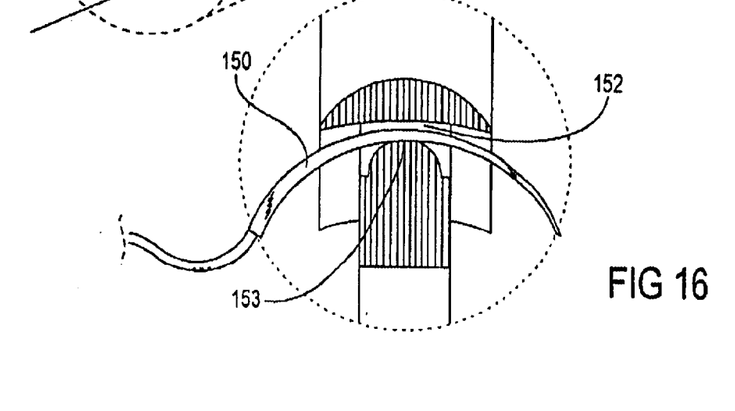
FIG. 16 is a front view of the needle gripper of the invention showing a curved suture needle contained therein.
Figure 17:
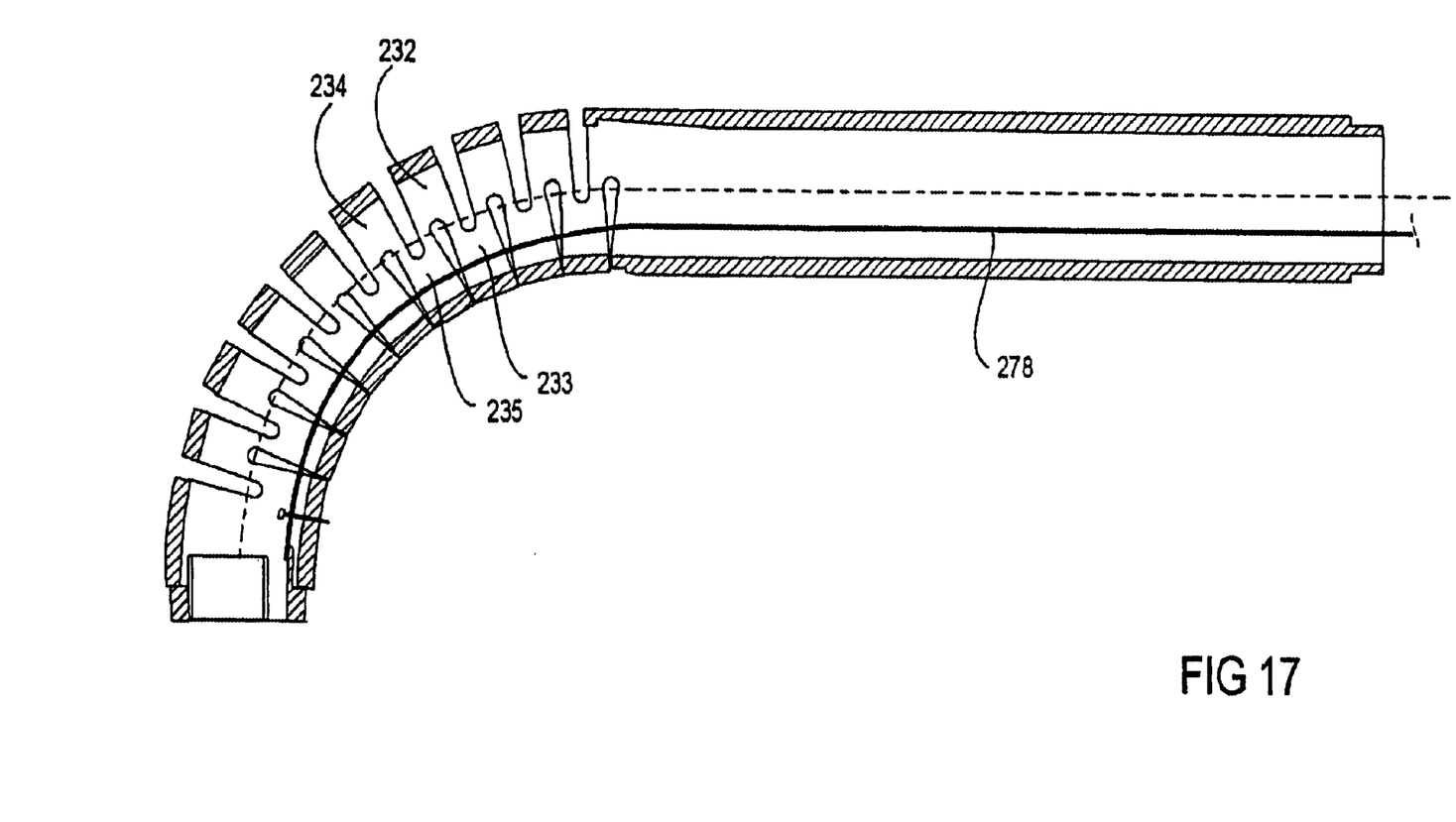
FIG. 17 is a side cut-away view of the articulated section of an embodiment of the invention in curved configuration.

In the interior of the tube 121 there may be an elastomeric sleeve 112 of friction reducing plastic, for example TEFLON®. Since, as described below, a push/pull wire 108 and a torque transmitting sheath 106, as well as cable 78 may all move within the limited space within tube 121, a friction reducing sleeve is generally helpful. The articulated section 120 may be formed by the segmented tube 121 of a super elastic and flexible metal such as nitinol having shape memory and flexibility. Alternatively, it may be in the form of any number of articulated tube structures as known in the art. In the case of the segmented tube 121, when the cable 78 is relaxed, the tube forming the articulated section naturally reverts to some preselected a configuration such as a relatively straight configuration. It may be altered in configuration by tightening the cable which compresses one side of the tube to increase curvature of the articulated section, such curvature is illustrated in FIG. 16, wherein a segmented tube having ribs 232,233,234,235 that are slightly offset with respect to each other, is compressed on one side by the retraction of cable 278. When the cable is relaxed, the tube returns to its prestressed shape (not shown).

The segmented tube may be attached to the elongate shaft 100 by means of a transitional tube 208 encasing the unsegmented length 122 of the articulated segment and the distal end 206 of the elongate shaft 100. Alternatively, the unsegmented portion of the segmented tube may be configured to fit within the tube of the elongate shaft (not shown), or to fit over the exterior of that tube (not shown) to join the two lengths.

Figure 6:
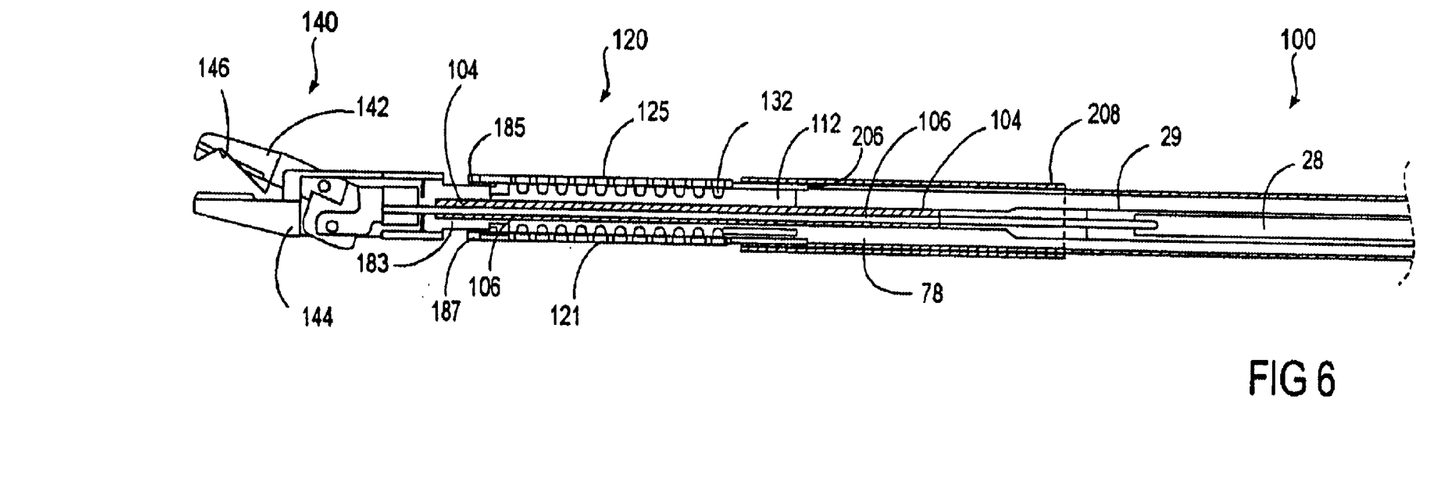
FIG. 6 is an enlarged cross-sectional view of a portion of the shaft and the needle gripper of an embodiment of the invention.

Within the elongate shaft is contained tension rod 28 and torque transmitting tube 29. Referring in general to FIG. 6, the tension rod 28 is attached at its distal end to a shielded cable 104. The torque transmitting tube 29 is attached at its distal end to torque transmitting flexible sheathing 106. The torque transmitting sheathing may be, for example, braided wire or mesh. When the articulated section is curved, the shielded cable and flexible sheathing function to transmit reciprocating motion from the tension rod 28 and rotational motion from the torque transmitting tube 29 to the effector unit 140 as described hereafter.

Figure 12:
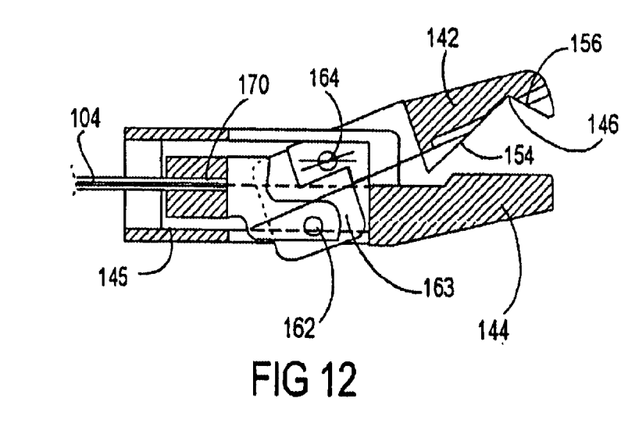
FIG. 12 is a cut-away view taken along line A—A in FIG. 11.
Figure 13:
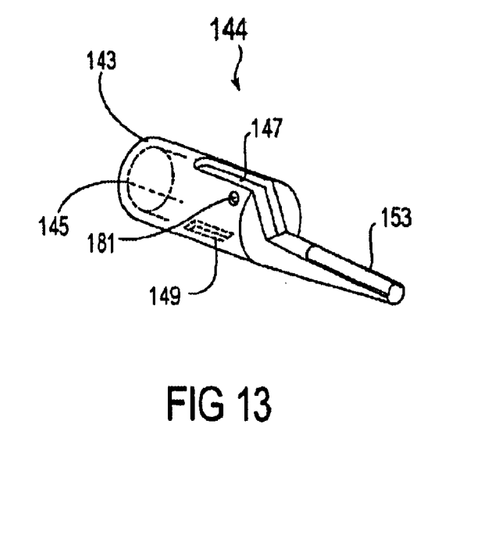
FIG. 13 is a perspective view of the lower jaw of a needle gripper of an embodiment of the invention.
Figure 14:
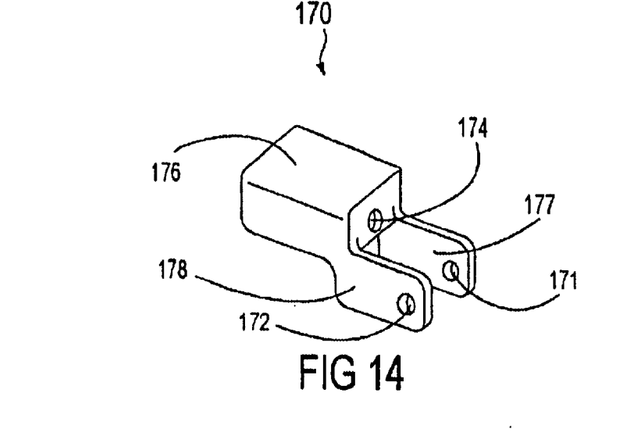
FIG. 14 is a top perspective drawing of the yoke of the needle gripper of an embodiment of the invention.
Figure 15:
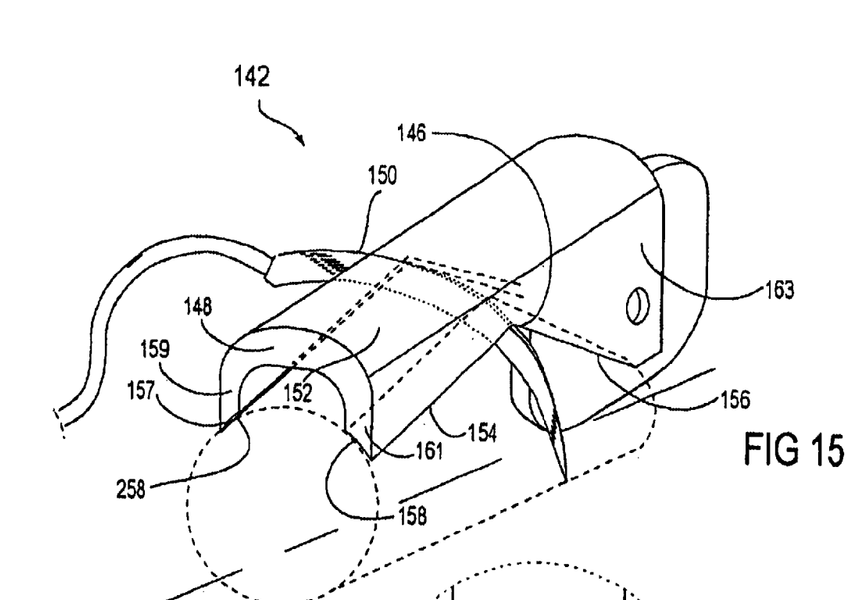
FIG. 15 is a top perspective view of the upper jaw of the needle gripper of an embodiment of the invention.

In the embodiment as illustrated in, for example, FIGS. 6 and 11–16, the effector unit 140 is a needle grasper for grasping a curved suture needle and automatically orienting the needle in a predetermined orientation. The needle grasper 140 comprises an upper jaw 142 and a lower jaw 144. The upper jaw is formed having a V-shaped side notch in its surface 146. Referring generally to FIGS. 11 through 16, the upper jaw has a generally U-shaped cross-section as shown at 148. The channel 152 at the apex of the notch 146 is sufficient to accommodate the curvature of a curved suture needle. The lower jaw as illustrated in FIG. 12 has a generally convex gripping surface 153. The radius of convexity is generally less than the radius of curvature of a suture needle to be used as illustrated in FIG. 15 at 150. In conjunction with the V-shaped notch in the upper jaw and the concave channel 152 within the upper jaw, the convex gripping surface 153 of the lower jaw serves to predictably orient a curved needle. A needle grasped generally between the upper and lower jaws of this needle gripper would tend to be forced along upwardly angled edge 154 or 156. At the same time the round surgical needle would tend to assume an orientation curved over the convex surface of the lower jaw and retained within concave channel 152 of the upper jaw. This results in a predictable orientation of the needle regardless of the angle at which the needle was initially grasped. This is particularly useful where the surgeon is attempting to orient the needle using endoscopic cameras or the like having little or no depth perception.

The lower edges of the sidewalls of the upper jaw 158, 258 are configured having a taper from the outer edge towards the inner edge. As a curved needle is gripped between the anvil and the upper jaw, it slides towards the apex 146 in the upper jaw. As it is sliding along the edges 158, 258, the taper acts to rotate the needle so that its curvature is generally pointed down. In conjunction with the convex gripping surface on the lower jaw, these two configurations act in concert to align the curved suture needle.

Referring generally to FIGS. 1, 6 and 11 through 16, the effector unit may be in the form of a needle gripper. The needle gripper as shown in the embodiment illustrated may be opened and closed by the reciprocating action of tension rod 29 transmitted through the articulated section 120 by cable 104. The means by which the needle gripper acts to orient a curved suture needle in a predetermined orientation is set forth above. This requires that the upper jaw of the needle gripper 142 be opened relative to the lower jaw of the needle gripper 144, receive a curved suture needle between the jaws, and then have the jaws close relative to each other and pinch the curved needle between them.

As stated, the needle gripper has an upper jaw 142, and a lower jaw 144 and further involves a yoke 170. The lower jaw has a generally tubular reward portion 143 which contains a generally cylindrical cavity therein 145. The surface of the lower jaw immediately above the cylindrical cavity therein has a slot 147. On the lower surface there is located another slot 149. There is hole 181 formed in the upper portion of the lower jaw, and a complimentary hole in the facing surface (not shown). The forwardly projecting lower portion of the lower jaw has a convex gripping surface 153.

The needle gripper yoke 170, as in FIG. 14, has a rear body portion 176 that has a tubular passage therethrough 174. At the forward portion of the yoke are two support plates 177, 178, each of which has a hole therethrough 171, 172.

Referring specifically to FIG. 15, the upper jaw 142 has a generally U-shaped cross section with side walls 159, 161 and a channel 152 extends therebetween. The side walls 163 of the upper jaw have a generally upwardly pointed V-shape, with a forward driving wedge 154 and a reward driving wedge 156 which are joined at apex 146. Lower edges of the sides 157, 158 are generally conically tapered inwardly. At the rear of the upper jaw are pivot plates 163.

When assembled as shown in FIG. 12, the distal end of push/pull cable 104 is secured within tubular passage 174. The yoke is contained within the cavity 145 in the reward section 143 of the lower jaw 144. The two pivot plates of the upper jaw, 163 and its compliment (not shown) are located within slot 147. The upper jaw is pivotally attached to the lower jaw by placing pivot pin 164 through hole 181 and the complimentary holes in the upper jaw. The yoke is pivotally attached to the upper jaw by a pin through the pivot plates of the upper jaw 163 and the support plates 177, 178 of the yoke. As can be most clearly seen in FIG. 12, the yoke 170 is dimensioned smaller than the cavity 145 in the lower jaw. When push/pull cable 104 is pulled rearwardly, it pulls the yoke which in turn pulls the upper jaw at a pin 162. This serves to rotate the upper jaw around a pin 164 while allowing rotation at the pin 162. This acts to close the channel in the upper jaw down over the convex gripping surface of the lower jaw. The reverse action of the push/pull cable 104 serves to open the jaws of the needle gripper 140. If the lower rear corner of the pivot plates is caused by this action to extend below the surface of the interior cavity 145, the slot 149 permits the corner to extend out and thus permits this motion.

Referring generally to FIG. 6, a rotation collar 183 is attached to torque transmitting mesh 106 at the distal end 206 of the tube 100. The rotation collar is affixed around its outer periphery to the internal surface of the cavity 145 in the lower jaw. When the torque transmitting tube 29 is rotated and in turn rotates the torque transmitting mesh, this acts to rotate the rotational collar and thus the effector unit 140. A bearing 185 may be provided to facilitate rotating at the distal end of the articulated section 120. This bearing may also attach to the distal end of the tension wire 78 so that when the tension wire is tightened, is acts to curve the articulated section.

Referring again to FIGS. 1 and 6, in practice, the surgeon may grasp the surgical tool with rotational capability by the gripper levers 12, 14, and may cause rotation of the effector unit by rotating the handle 10. The rotational motion of handle rotates the carrier 52 which, in turn, rotates the planetary housing 62 which contains ring gear 66. The ring gear's teeth are meshed with the teeth of the planetary gears 65, 66, and 67, which planetary gears are meshed on their other side with the gun gear 68. This turning the handles effects a turning of the sun gear. In the embodiment shown, the sun gear is attached to and rotates the torque transmitting tube 29 with a ratio of 4:1 to the rotation of the handle. This rotational motion is carried via the torque transmitting tube 29 to the torque transmitting mesh 106 covering the cable shielded cable 104. The outer mesh of the shielded cable 104 in turn transmits the torque to the effector unit 140 and rotates the effector unit, for example, a needle grasper, in direct response to the rotational action of the surgeon's hands. Although the ratio of motion is 4:1, the timing of the rotation, the feel of direct contact between hands and effector unit, the coordination of the turning motion with pushing and pulling motion, and other similar kinesthetic effects permit the surgeon to directly and dynamically manipulate the effector unit to perform various functions, for example, suturing, while at the same time keeping the surgeon's forearms relatively still. Likewise, the surgeon may directly cause reciprocating motion of the tension rod 28 by squeezing the handles 10, 12 which acts to pull the tension rod head rearwardly, retracting the tension rod through the various bearings and, ultimately, retracting the shielded cable which acts to open and close the jaws of the needle gripper.

As shown in FIGS. 12, 15 and 16, the surgeon may position a curved suture needle 150 between the open jaws 142, 144 of the needle gripper and close those jaws around the needle. The configuration of the needle gripper having an upper jaw with an apex 146 and conically tapered upper jaw edges 158, 258, in combination with a lower jaw having a convex grasping surface 153 acts to grasp the needle, slide it upward to the apex in the upper jaw, while simultaneously and automatically orienting the needle perpendicular to the needle gripper with the curved needle 150 pointing downward. In conjunction with the rotational motion possible by action of the rotational motion translator 50, a suturing motion is thereby facilitated. Note that while the directional terms upper, lower, downward and the like, are used, such relative terms are descriptive only and in no way limit the disclosure.

While a particular form of the invention has been illustrated and described, it will be apparent that various modifications can be made without departing from the spirit and scope of the invention.

What is claimed is:

1. A surgical instrument comprising:

a rotatable handle;

a rotatable effector unit; and a rotational motion translator coupled to said rotatable handle and said rotatable effector unit, said rotational motion translator to translate rotational motion from said rotatable handle to said rotatable effector unit in a non 1:1 ratio, when said rotatable handle is rotated.

2. The surgical instrument of claim 1 wherein said rotational motion translator is a Planetary Gear Mechanism comprising:

an outer ring gear coupled to said handle;

a sun gear coupled to said effector unit; and at least one planetary gear disposed between said ring gear and said sun gear.

3. The surgical instrument of claim 1 further comprising:

an elongated shaft disposed between said rotatable effector unit and said rotational motion translator; and a torque transmission tube interior of said shaft and coupled to said rotatable effector unit and said rotational motion translator.

4. The surgical instrument of claim 3 further comprising a tension bar interior of said shaft and coupled to said handle and said rotatable effector unit to effect a non-rotatable force upon said rotatable effector unit.

5. The surgical instrument of claim 3 further comprising:

an articulation section of said shaft;

an adjustment cable coupled to said shaft distal and articulation section; and an adjustment knob coupled to said shaft proximal said articulation section, said adjustment knob coupled to said adjustment cable and to effect articulation of said articulation section.

6. The surgical instrument of claim 5 wherein said articulation section includes a slotted tube comprising a plurality of ribs with cutouts therebetween to allow flexure of said articulation section.

7. The surgical instrument of claim 6 wherein said rotatable effector unit is a needle gripper.

8. The surgical instrument of claim 7 further comprising:

a first jaw having a concave portion; and a second jaw having a convex portion, said concave portion and said convex portion to cooperate in securing a curved needle.

9. A surgical method comprising:

providing a surgical instrument having a rotatable effector unit and a rotatable handle with a rotational motion translator coupled to said rotatable effector unit;

advancing said surgical instrument to a surgical site to be effected by said rotatable effector unit; and rotating said rotatable handle; and translating said rotating from said handle to said rotatable effector unit in a non 1:1 ratio via said rotational motion translator.

10. The method of claim 9 further comprising articulating an articulation section of a shaft disposed between said rotatable effector unit said rotational motion translator after said advancing.

11. The method of claim 9 further comprising laterally moving a tension bar coupled to said handle and said rotatable effector unit to effect a non-rotatable force upon said rotatable effector unit after said advancing.

* * * * *

UNITED STATES PATENT AND TRADEMARK OFFICE
CERTIFICATE OF CORRECTION

PATENT NO.    : 6,663,641 B1
DATED         : December 16, 2003
INVENTOR(S)   : Kovac et al.

It is certified that error appears in the above-identified patent and that said Letters Patent is hereby corrected as shown below:

Column 13,
Line 7, please delete "claim 6" and insert -- claim 1 --.

Signed and Sealed this

First Day of June, 2004

JON W. DUDAS
*Acting Director of the United States Patent and Trademark Office*